United States Patent [19]

Oku

[11] Patent Number: 5,224,467
[45] Date of Patent: Jul. 6, 1993

[54] ENDOSCOPE WITH DIRECTION INDICATION MECHANISM

[75] Inventor: Toshio Oku, Tokyo, Japan

[73] Assignee: Kabushiki Kaisha Machida Seisakusho, Tokyo, Japan

[21] Appl. No.: 965,755

[22] Filed: Oct. 23, 1992

[30] Foreign Application Priority Data

Oct. 30, 1991 [JP] Japan .................. 3-311581

[51] Int. Cl.[5] .................................. A61B 1/00
[52] U.S. Cl. ............................. 128/4; 126/6
[58] Field of Search ......... 128/4, 6; 33/512, 399, 33/391, 402; 604/116, 118

[56] References Cited

U.S. PATENT DOCUMENTS

| | | | |
|---|---|---|---|
| 1,495,629 | 5/1924 | Arthur | 33/391 |
| 3,533,167 | 10/1970 | Thompson et al. | 33/399 X |
| 3,889,627 | 6/1975 | Cloyd | 33/402 X |
| 4,340,302 | 7/1982 | Oku | 128/4 X |
| 5,099,850 | 3/1992 | Matsui et al. | 128/4 X |

FOREIGN PATENT DOCUMENTS 62-63910 3/1987 Japan .
2-68024 3/1990 Japan .

Primary Examiner—Richard J. Apley
Assistant Examiner—Beverly A. Meindl
Attorney, Agent, or Firm—Fish & Richardson

[57] ABSTRACT

In order to confirm the direction of each portion of an image picked up by an endoscope, the endoscope includes a direction indication mechanism detachably mounted on a tip member. This direction indication mechanism includes an annular holder member which is held in contact with a front end face of the tip member and is arranged along a peripheral edge of an inspection window, and a displacement member supported by the holder member for displacement circumferentially of the holder member under the influence of gravity. The displacement member has a direction indication portion disposed radially inwardly of the inner peripheral edge of the holder member and the peripheral edge of the inspection widow. The direction indication portion is observed from the inspection window. When the direction indication function is not needed, the direction indication mechanism is detached from the tip member.

11 Claims, 4 Drawing Sheets

ENDOSCOPE WITH DIRECTION INDICATION MECHANISM

BACKGROUND OF THE INVENTION

This invention relates to an endoscope having a direction indication mechanism by which the actual direction of each portion of an image obtained by the endoscope can be confirmed.

Generally, an endoscope comprises a body, an insertion portion extending from the body, and a rigid tip member mounted on a distal end of the insertion portion. An inspection window is provided at a distal end face of the tip member. An image entering from the inspection window is observed from an ocular portion of the body through an image guide passing through the insertion portion.

When the insertion portion of the endoscope is inserted into a tube of a complicated shape so as to observe the inner surface of this tube, the actual direction of each portion of an image obtained or picked up by the endoscope is not confirmed, for example, because of a torsion of the insertion portion. Therefore, even if a defect can be found on the inner surface of the tube, the direction in which this defect exists (that is, whether the defect is in the right, the left, the upper or the lower direction) is not confirmed.

In order to overcome such a disadvantage, there have been proposed endoscopes, as disclosed in Japanese Laid-Open Patent Application Nos. 62-63910 and 2-68024, which incorporate a direction indication mechanism for confirming the actual direction of each portion of a picked-up image.

The direction indication mechanism of the former publication is provided within a tip member of the endoscope as shown in FIGS. 1 and 3 of this publication, and more specifically this mechanism is disposed between an inspection window and a distal end of an image guide, and has a ball 12 which is limited in axial movement by a pair of transparent plates 11 but is movable in circumferential and radial directions. Therefore, part of this ball can be observed as part of an image from an ocular portion provided on a body of the endoscope. The ball is always located at the lower side by gravity, and therefore the upper and lower directions with respect to the image can be confirmed by observing the ball. In embodiments shown in FIGS. 8 and 9 of this publication, there is used a transparent disk 15 rotatably supported by an annular bearing 14. The center of gravity of this disk 15 is eccentric from the axis of rotation thereof, and a direction indication mark 16 is provided on that portion of this disk always kept at the lower side. In the endoscope disclosed in this publication, however, since the direction indication mechanism is provided between the inspection window and the distal end of the image guide, this mechanism can not be detached. Therefore, even when the direction indication is not needed, the field of vision is narrowed by the ball 12 and the mark 16, so that the observation can not be carried out satisfactorily.

The direction indication mechanism disclosed in the latter publication includes a forwardly-extending wire 26 secured to a tip member of the endoscope, and a weight 28 secured to a distal end of this wire. The wire is elastically deformed by the weight. The direction of deformation of the wire is the direction of the gravity, and by observing this, the upper and lower directions with respect to the image can be confirmed. In the direction indication mechanism of this publication, there has been encountered a problem that since the wire hangs down across the field of vision, the image can not be observed satisfactorily. This publications show in FIGS. 1, 4, 6 and 9 embodiments in which the proximal portion of the wire is releaseably connected to the tip member.

SUMMARY OF THE INVENTION

It is an object of this invention to provide an endoscope in which the upper and lower directions with respect to an image obtained by the endoscope can be confirmed, and when the direction does not need to be confirmed, the image can be observed with a wide field of vision.

According to the present invention, there is provided an endoscope comprising:

(a) a body;

(b) a flexible insertion portion extending from a front end of the body;

(c) a rigid tip member mounted on a front end of the insertion portion, the tip member having an inspection window and an illumination window formed at a front end face thereof; and (d) a direction indication mechanism detachably mounted on the tip member, the direction indication mechanism comprising annular holder means which is held in contact with the front end face of the tip member and is arranged along a peripheral edge of the inspection window, and a displacement member which is supported by the holder means for displacement circumferentially of the holder means under the influence of gravity, and the displacement member having a direction indication portion disposed radially inwardly of an inner peripheral edge of the holder means and the peripheral edge of the inspection window.

DESCRIPTION OF THE PREFERRED EMBODIMENTS

Figure 1:
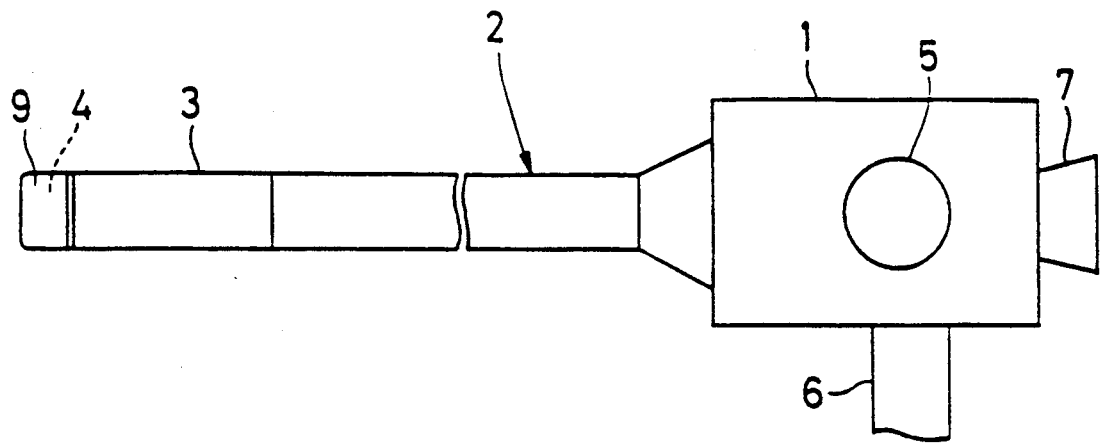
FIG. 1 is a view showing an overall construction of an endoscope provided in accordance with the present invention.
Figure 2:
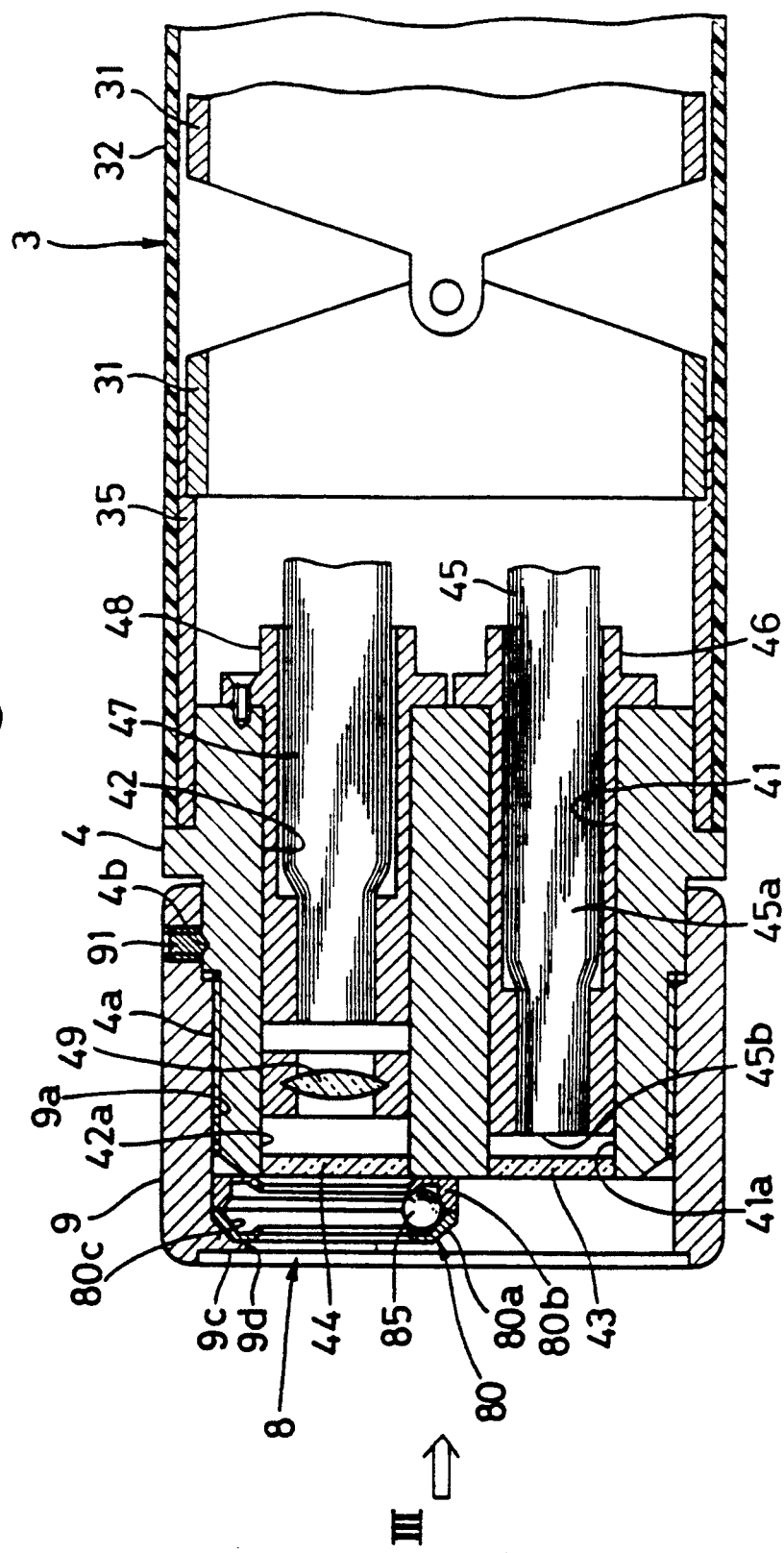
FIG. 2 is an enlarged cross-sectional view of a front end portion of the endoscope.

The present invention will now be described with reference to the drawings. As shown in FIG. 1, an endoscope comprises a body 1, and a flexible insertion portion 2 extending from the body 1. The front end portion of the insertion portion 2 serves as a bending portion 3, and a rigid tip member 4 is mounted on the front end of this bending portion 3. As shown in FIG. 2, the bending portion 3 comprises a row of tubular segments 31 pivotally connected to one another, and a tube 32 covering the outer peripheries of these segments 31. The foremost segment 31 is connected to the tip member 4 through a connection tube 35. The foremost segment 31 is also connected to a manipulation member 5, mounted on the body 1, by one or more wires passing through the insertion portion 2 so that the bending portion 3 can be remotely operated to be bent by the manipulation member 5.

Figure 3:
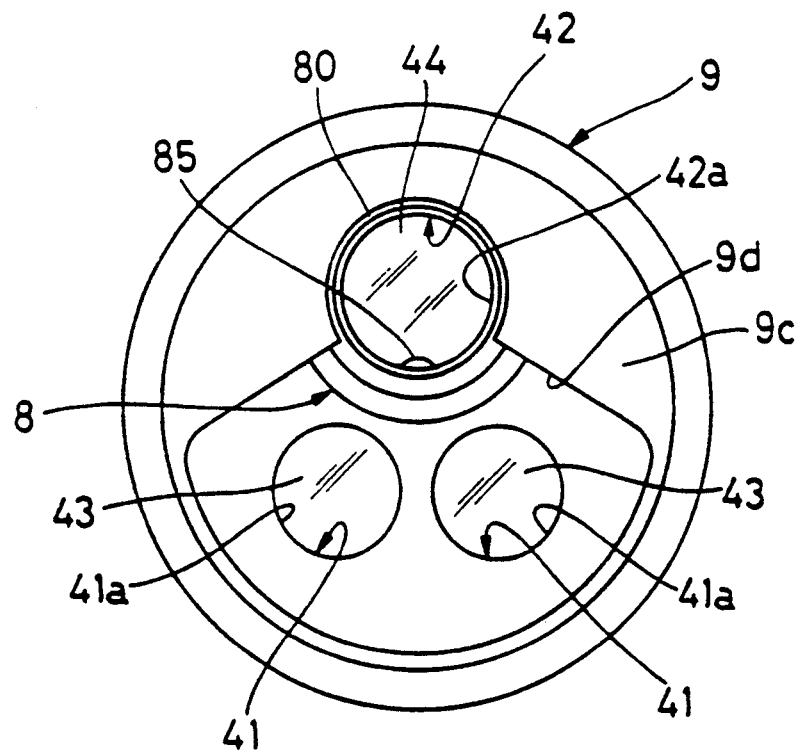
FIG. 3 is a view taken as seen from a direction III of FIG. 2.

As shown in FIGS. 2 and 3, two first through holes 41 and a second through hole 42 are formed axially through the tip member 4. The front open end of each of the two first through holes 41 serves as an illumination window 41a, and the front open end of the second through hole 42 serves as an inspection window 42a. Transparent plate 43 and 44 are fitted in each illumination window 41a and the inspection window 42a, respectively.

Support tubes 46 are fitted in and fixed to the two first through holes 41, respectively, and support two branch portions 45a of an optical fiber bundle 45, respectively. The front end face 45b of each branch portion 45a of the optical fiber bundle 45 faces the transparent plate 43 in the corresponding illumination window 41a. The optical fiber bundle 45 extends through the insertion portion 2, the body 1 and a cable 6 extending from the body 1, and is optically connected at its rear end to a light source (not shown). With this arrangement, light from this light source is applied from the illumination windows 41a.

A support tube 48 is fitted in and fixed to the second through hole 42, and supports a front end portion of another optical fiber bundle 47. The front end face of the optical fiber bundle 47 faces the transparent plate 44 of the inspection window 42a through an objective lens 49. The rear end of this optical fiber bundle 47 faces an ocular lens (not shown) housed in a ocular portion 7 on the body 1, so that the observation from the ocular portion 7 is possible. The endoscope may be of the type connectable to a television set, in which case an image sensor such as CCD is provided in facing relation to the objective lens 49.

A direction indication mechanism 8 of an annular shape is detachably mounted on the tip member 4. This direction indication mechanism 8 comprises an annular holder member 80 which is held in contact with the front end face of the tip member 4 and is arranged along the peripheral edge of the inspection window 42a, and a ball of steel (displacement member) 85 supported by the holder member 80 for displacement circumferentially of the holder member 80 under the influence of gravity. The inner peripheral edge of the holder member 80 generally coincides with the peripheral edge of the inspection window 42a. The holder member 80 is composed of a pair of ring-like halves 80a and 80b of a L-shaped cross-section connected together, and has an annular groove 80c which is radially inwardly open. The ball 85 is received in the groove 80c in such a manner as not to be disengaged therefrom, and part of this ball 85 is projected radially inwardly from the inner peripheral edge of the holder member 80 and the inner edge of the inspection window 42a, and serves as a direction indication portion.

The direction indication mechanism 8 is attached to the tip member 4 by a tubular retainer 9. More specifically, a threaded portion 9a is formed on the inner peripheral surface of the retainer 9, and this threaded portion 9a is threaded on a threaded portion 4a formed on the outer periphery of the tip member 4 to secure the retainer 9 to the tip member 4. The retainer 9 is held in position and prevented from rotation by a screw 91 passing through the peripheral wall of the retainer 9 into a recess 4b formed in the outer peripheral surface of the tip member 4. A radially inwardly-extending flange 9c is formed on the front end of the retainer 9. The holder member 80 of the direction indication mechanism 8 is held between the flange 9c of the retainer 9 and the front end face of the tip member 4. As shown in FIG. 3, an opening 9d corresponding to the illumination windows 41a and the inspection window 42a is formed in the flange 9c.

For inspecting an inner side of a tube by the endoscope 1 of the above construction, the insertion portion 2 of the endoscope 1 is inserted into this tube, and the inner surface of the tube is observed from the inspection window 42a to check whether there is any flaw on this inner surface. The ball 85 of the direction indication mechanism 8 is always located at the lower side under the influence of gravity, and part of the ball 85 is projected radially inwardly from the inner peripheral edge of the holder member 80 and the peripheral edge of the inspection window 42a, and therefore can be viewed from the inspection window 42a. Namely, the image observed from the inspection window 42a includes part of the ball 85 which indicates the lower direction. Therefore, when a flaw is found, the direction in which this flaw is located can be confirmed. In the observation of this image, part of the steel ball 85 is disposed at the peripheral edge portion of the image, and therefore this direction indication mechanism 8 will not much affect the observation of the image, as compared with the conventional direction indication mechanism of the type using a wire.

When the direction indication is not needed, the screw 91 is loosened, and the retainer 9 is turned to be detached from the tip member 4, thereby removing the direction indication mechanism 8 from the tip member 4. By doing so, the image is prevented from being partially intercepted by the steel ball 85, and therefore the observation as obtained with an endoscope of an ordinary type can be achieved.

Next, other embodiments of the present invention will now be described. Those portions of these embodiments corresponding to those of the preceding embodiment are designated by identical reference numerals, respectively, and detailed explanation thereof will be omitted.

Figure 4:
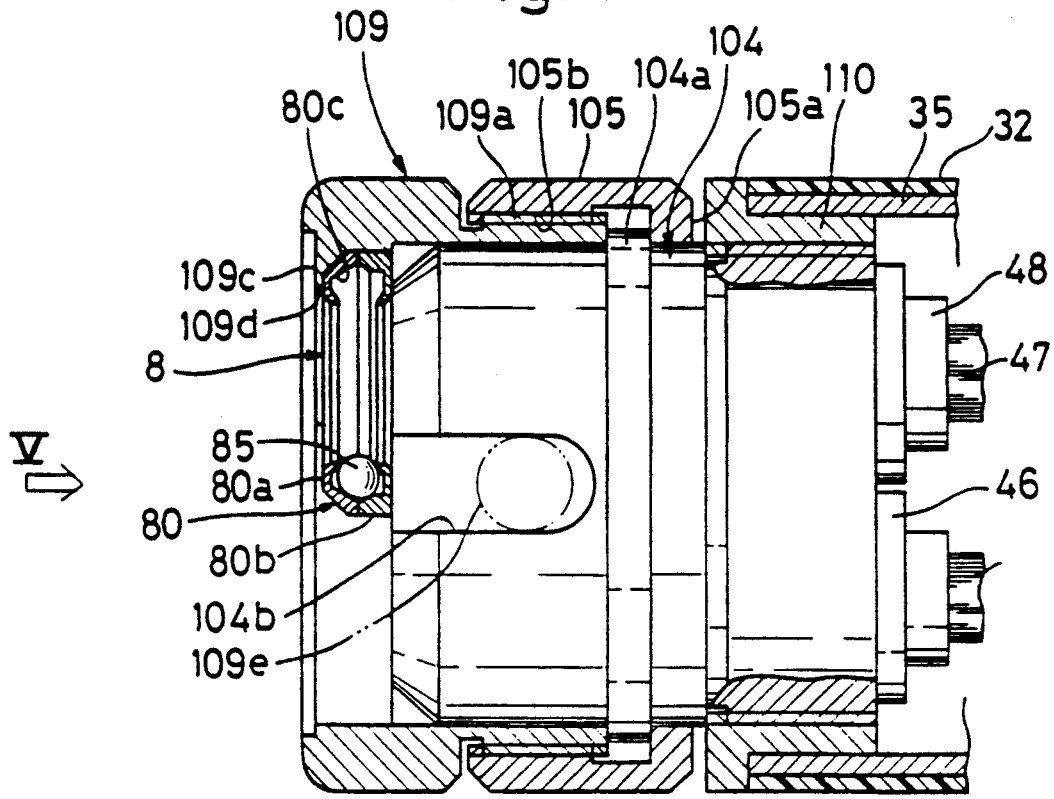
FIG. 4 is an enlarged cross-sectional view of a front end portion of a modified endoscope.
Figure 5:
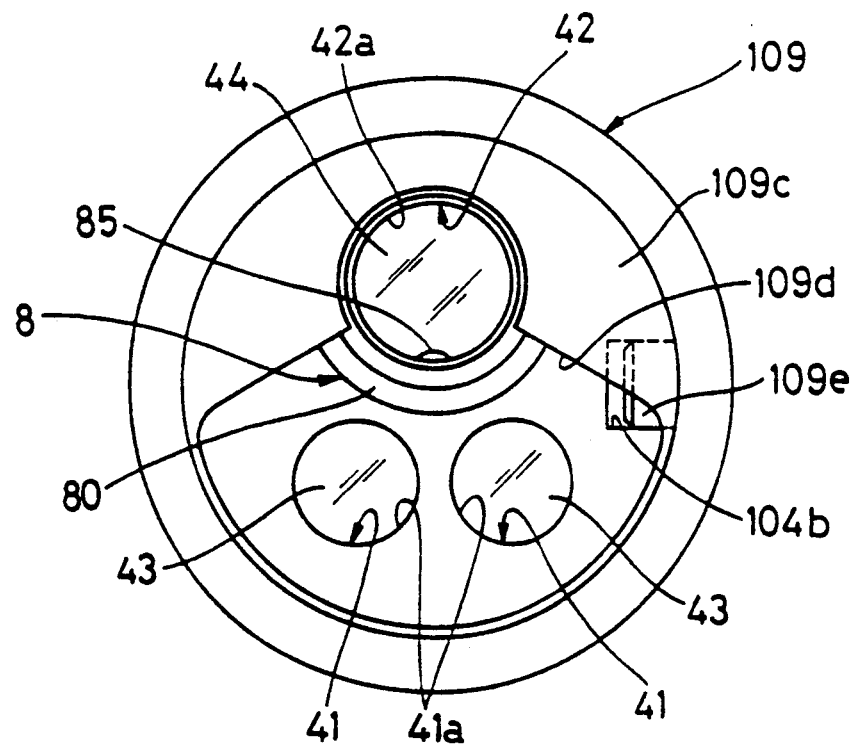
FIG. 5 is a view as seen from a direction V of FIG. 4.

In the embodiment shown in FIGS. 4 and 5, a structure for attaching a direction indication mechanism 8 to a tip member 104 is different from that in the preceding embodiment. More specifically, a threaded portion is not formed on the outer periphery of the tip member 104, and an annular projection 104a is formed on this outer periphery. A first tubular retainer 105 is mounted on the outer periphery of the tip member 104. A radially inwardly-extending projection 105a of an annular shape is formed on the rear end of the first retainer 105. This projection 105a is abutted against the projection 104a of the tip member 104 to thereby prevent the first retainer 105 from moving axially forwardly. A threaded portion 105b is formed on the inner peripheral surface of the front end portion of the first retainer 105. A second retainer 109 has a threaded portion 109a formed on an outer peripheral surface of a rear end portion thereof. A flange 109c having an opening 109d similar in shape to the opening 9d in the preceding embodiment is formed on the front end of the second retainer 109. An axially-extending groove 104b is formed in the outer periphery of the front end portion of the tip member 104. A radially inwardly-extending key 109e is formed on the inner periphery of the rear end portion of the second retainer 109. The threaded portion 109a of the second retainer 109 is threaded in the threaded portion 105b of the first retainer 105, and the key 109e is received in the groove 104b, and in this condition when the first retainer 105 is rotated, the second retainer 109 is moved axially rearwardly without rotation in such a manner that the opening 109d is kept corresponding to the illumination window 41a and the inspection window 42a. As a result, the direction indication mechanism 8 is releaseably held between the flange 109c of the second retainer 109 and the front end face of the tip member 104.

In this embodiment, a threaded tube 110 is fixedly secured to a front end portion of a connection tube 35, and this threaded tube 110 is threaded on the rear end portion of the tip member to thereby attach the connection tube 35 to the tip member 104.

Figure 6:
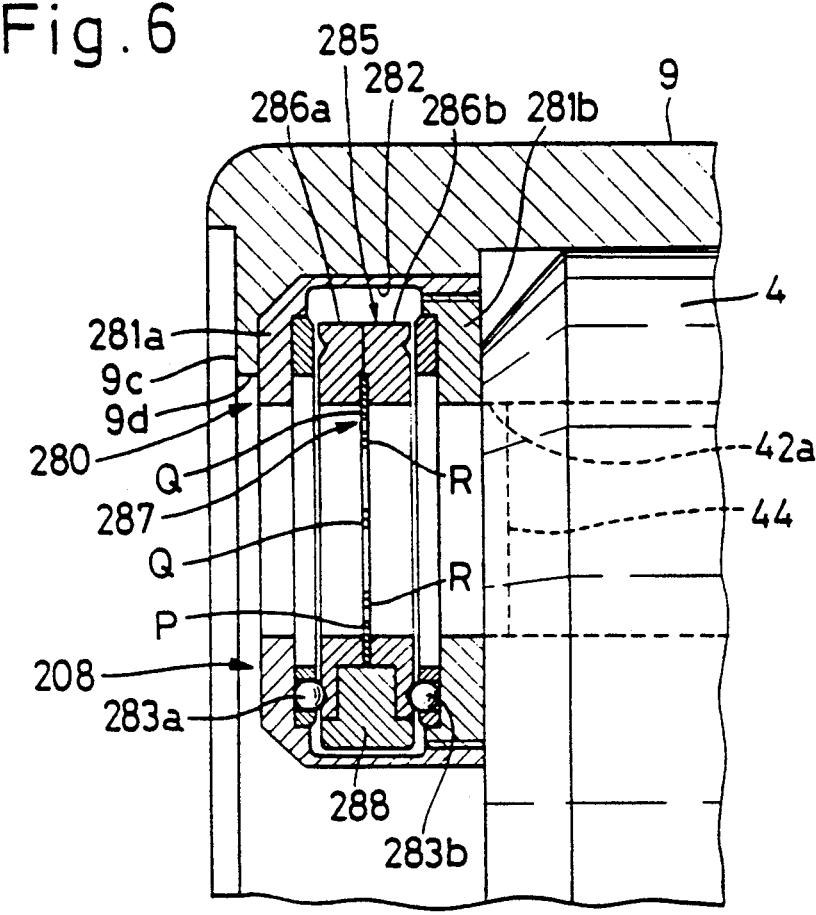
FIG. 6 is an enlarged cross-sectional view of a front end portion of another modified endoscope.
Figure 7:
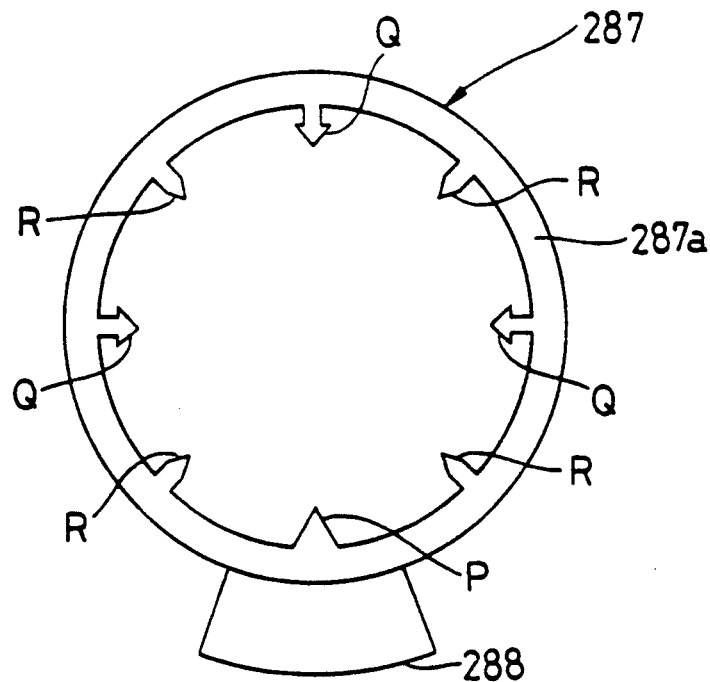
FIG. 7 is a front-elevational view of a direction indication sheet used in the endoscope of FIG. 6.

A direction indication mechanism 208 shown in FIGS. 6 and 7 comprises annular holder means 280, and an annular displacement member 285 rotatably supported by the holder means 280. The holder means 280 comprises a pair of annular holders 281a and 281b threadedly connected together, and a pair of annular bearings 283a and 283b provided respectively on opposed side surfaces of an annular recess 282 formed by the pair of holders 281a and 281b. The displacement member 285 comprises a pair of ring-like halves 286a and 286b which are connected together by screws (not shown) and are rotatably supported by the bearings 283a and 283b, and a direction indication sheet 287 supported by the halves 286a and 286b, the direction indication sheet 287 being in the form of a thin annular sheet. A weight 288 is fixedly secured to predetermined portions of the outer peripheries of the halves 286a and 286b, so that the center of gravity of the displacement member 285 is eccentric from the axis of rotation thereof. The direction indication sheet 287 is disposed in a plane perpendicular to an axis of a tip member 4. The direction indication sheet includes a circular base 287a, and three kinds of projections P, Q and R which have different shapes from one another and extend radially inwardly from the inner periphery of the circular base 287a. The base 287a of the direction indication sheet 287 is sandwiched between and supported by the pair of halves 286a and 286b, and the inner periphery of the base 287a coincides with the inner peripheral surfaces of the halves 286a and 286b, so that only the projections P, Q and R are projected from these inner peripheral surfaces. The axis of rotation of the displacement member 285 is aligned with the axis (the center) of the base 287a and the axis (the center) of an inspection window 42a. One projection P of the direction indication sheet 287 is disposed in registry with the weight 288, and is always located at the lower side. The three projections Q are circumferentially spaced 90° and 180° from the projection P, that is, are disposed at the right, the left and the upper side, respectively. The four projections R are circumferentially spaced 45° from the projections P and Q, that is, are disposed at the obliquely upper right, the obliquely lower right, the obliquely upper left and the obliquely lower left, respectively.

The present invention is not limited to the above embodiments, and various modifications can be made.

What is claimed is:

1. An endoscope comprising:
   (a) a body;
   (b) a flexible insertion portion extending from a front end of said body;
   (c) a rigid tip member mounted on a front end of said insertion portion, said tip member having an inspection window and an illumination window formed at a front end face thereof; and
   (d) a direction indication mechanism detachably mounted on said tip member, said direction indication mechanism comprising annular holder means which is held in contact with the front end face of said tip member and is arranged along a peripheral edge of said inspection window, and a displacement member which is supported by said holder means for displacement circumferentially of said holder means under the influence of gravity, and said displacement member having a direction indication portion disposed radially inwardly of an inner peripheral edge of said holder means and the peripheral edge of said inspection window.

2. An endoscope according to claim 1, further comprising a tubular retainer threaded on an outer peripheral surface of said tip member, said retainer having a radially inwardly-directed flange formed on a front end thereof, and said holder means of said direction indication mechanism being held between said flange of said retainer and the front end face of said tip member.

3. An endoscope according to claim 2, in which said flange has an opening corresponding to said inspection window and said illumination window.

4. An endoscope according to claim 1, further comprising a first tubular retainer which is rotatably mounted on said tip member in such a manner that an axial movement of said first retainer is limited, and a second tubular retainer threadedly engaged with said first retainer, said second retainer having a radially inwardly-directed flange formed on a front end thereof, and said holder means of said direction indication mechanism being held between said flange of said second retainer and said front end face of said tip member.

5. An endoscope according to claim 4, in which said flange has an opening corresponding to said inspection window and said illumination window, an axially-extending groove being formed in an outer peripheral surface of said tip member, a radially inwardly-projecting key being formed on an inner peripheral surface of said second retainer, said key being received in said groove, so that said second retainer is unable to rotate relative to said tip member but is allowed to move axially of said tip member.

6. An endoscope according to claim 1, in which said holder means having an annular groove which is open radially inwardly, said displacement member being in the form of a ball, said ball being received in said groove, and part of said ball projecting radially inwardly from the inner peripheral edge of said holder means and the peripheral edge of said inspection window to serve as said direction indication portion.

7. An endoscope according to claim 1, in which said displacement member has an annular shape, and is rotatably supported by said holder means, the center of gravity of said displacement member being eccentric from the axis of rotation thereof.

8. An endoscope according to claim 7, in which said displacement member has a weight mounted on a predetermined portion of an outer periphery of said displacement member.

9. An endoscope according to claim 7, in which said displacement member has a direction indication sheet disposed in a plane perpendicular to the axis of said tip member, said direction indication sheet including an annular base, a projection extending radially inwardly from said base, and said projection serving as said direction indication portion, and the axis of rotation of said displacement member being aligned with the center of said base and the center of said inspection window.

10. An endoscope according to claim 9, in which said holder means comprises a pair of ring halves connected together, said base of said direction indication sheet being held between said pair of ring halves, and said projection projecting radially inwardly from inner peripheral surfaces of said ring halves.

11. An endoscope according to claim 10, in which said projection is located in the direction of eccentricity of said gravity center, and represents a lower direction, and said direction indication sheet further has three projections which are circumferentially spaced 90° and 180° from said first-mentioned projection and project radially inwardly from said base, said three projections being different in shape from said first-mentioned projection.

* * * * *